US009417171B2

(12) United States Patent
Takemura et al.

(10) Patent No.: US 9,417,171 B2
(45) Date of Patent: Aug. 16, 2016

(54) HARDNESS TESTER

(71) Applicant: MITUTOYO CORPORATION, Kanagawa (JP)

(72) Inventors: Fumihiro Takemura, Brussels (BE); Fumihiko Koshimizu, Zama (JP)

(73) Assignee: MITUTOYO CORPORATION, Kanagawa (JP)

( * ) Notice: Subject to any disclaimer, the term of this patent is extended or adjusted under 35 U.S.C. 154(b) by 517 days.

(21) Appl. No.: 13/828,164

(22) Filed: Mar. 14, 2013

(65) Prior Publication Data

US 2013/0255362 A1    Oct. 3, 2013

(30) Foreign Application Priority Data

Mar. 27, 2012  (JP) ................. 2012-070584

(51) Int. Cl.
*G01N 3/48*   (2006.01)
*G01N 3/42*   (2006.01)

(52) U.S. Cl.
CPC .......... *G01N 3/42* (2013.01); *G01N 2203/0003* (2013.01); *G01N 2203/008* (2013.01); *G01N 2203/0019* (2013.01)

(58) Field of Classification Search
CPC ... G01N 3/42; G01N 2203/0286; G01N 3/40; G01N 2203/0082; G01N 2203/0682
USPC ...................................... 73/78, 81
See application file for complete search history.

(56) References Cited

U.S. PATENT DOCUMENTS

| | | | | |
|---|---|---|---|---|
| 3,949,600 A | * | 4/1976 | Iwasaki .................... | G01N 3/44 73/83 |
| 5,904,658 A | * | 5/1999 | Niederauer .......... | A61B 5/0053 600/587 |
| 6,142,010 A | * | 11/2000 | Merck, Jr. ................ | G01N 3/42 73/81 |
| 6,641,893 B1 | * | 11/2003 | Suresh .................... | C03C 14/00 428/105 |
| 7,379,173 B2 | * | 5/2008 | Fairley ................... | G01N 21/21 356/237.4 |
| 7,554,655 B2 | * | 6/2009 | Fairley ............... | G01N 21/8806 356/237.4 |
| 8,401,339 B1 | * | 3/2013 | Anderson ............... | G06K 9/36 382/298 |
| 2006/0288763 A1 | * | 12/2006 | Tsujii ....................... | G01N 3/42 73/81 |
| 2010/0126257 A1 | * | 5/2010 | Brougher ................. | G01N 3/42 73/81 |
| 2012/0085154 A1 | | 4/2012 | Takemura et al. | |
| 2012/0087567 A1 | | 4/2012 | Takemura et al. | |
| 2013/0047712 A1 | | 2/2013 | Ariga et al. | |

FOREIGN PATENT DOCUMENTS

| | | | |
|---|---|---|---|
| JP | 2004-286541 A | | 10/2004 |
| JP | 2004286541 A | * | 10/2004 |

OTHER PUBLICATIONS

U.S. Appl. No. 13/832,631 to Fumihiro Takemura et al., filed Mar. 15, 2013.

* cited by examiner

*Primary Examiner* — Eric S McCall
*Assistant Examiner* — Mohammed E Keramet-Amircola
(74) *Attorney, Agent, or Firm* — Greenblum & Bernstein, P.L.C.

(57) ABSTRACT

A hardness tester capable of facilitating positioning of a sample even when the hardness tester includes a manual XY stage. The hardness tester includes an XY stage displacing a sample stage in a horizontal direction; a CCD camera capturing an image of a sample surface via an objective lens; a monitor displaying the image of the sample surface captured by the CCD camera; an operator specifying a test position at which an indentation is to be formed, the test position being specified on the image displayed on the display; and a CPU calculating, in conjunction with displacement of the XY stage, an amount of offset in the XY direction between the test position and a center position of the indenter when forming the indentation, then displaying the calculated amount of offset on the display.

8 Claims, 10 Drawing Sheets

HARDNESS TESTER

CROSS-REFERENCE TO RELATED APPLICATIONS

The present application claims priority under 35 U.S.C. §119 of Japanese Application No. 2012-070584, filed on Mar. 27, 2012, the disclosure of which is expressly incorporated by reference herein in its entirety.

BACKGROUND OF THE INVENTION

1. Field of the Invention

The present invention relates to a hardness tester.

2. Description of Related Art

Generally, a process to increase hardness of a surface is performed on metal components using a heat process in order to improve mechanical characteristics sought for the components. Then, a hardness test is performed to evaluate whether the hardness of the surface has attained the required hardness or whether a specified hardness has been obtained to a specific depth from the surface using the heat process.

Conventionally, hardness testing methods of a pressing type are well known, such as the Vickers hardness test and the Knoop hardness test, which employ a hardness tester in which an indenter having a planar polygonal shape is pressed against a surface of a sample, then a degree of hardness of the sample is measured from a length of a diagonal line in a resulting polygonal indentation in the sample surface. Such hardness testing methods are widely used in evaluating mechanical characteristics of metallic materials (see, e.g., Japanese Patent Laid-open Publication No. 2004-286541).

As is commonly known, the Vickers hardness test employs a quadrangular pyramid diamond indenter and indicates the degree of hardness by a relationship between an average value for the length of the two diagonal lines of the quadrangular pyramid indentation formed in the surface of the sample and a pressing load of the indenter on the sample. The Knoop hardness test employs a rhomboid pyramid diamond indenter and indicates the degree of hardness by a relationship between the length of the longer of the diagonal lines of the rhomboid pyramid indentation formed in the surface of the sample and the pressing load of the indenter on the sample.

Typically, when the hardness of a metal component (hereafter referred to as a sample) is evaluated with the hardness tester, a user determines a test position on the sample ahead of time, displaces an XY stage to position the sample such that an indentation will be formed in the desired test position, then performs a hardness testing process. As shown in FIG. 10, the test positions P are frequently specified at a predetermined pitch along straight lines L1, L2, and so on, which are oriented from an edge of a sample S toward a horizontal-direction interior of the sample S. Moreover, a shape of the sample S is complex. Therefore, the test positions P are specified along the straight lines L1, L2, and so on, which are oriented in various directions.

In the hardness tester that includes an automatically drive-controlled XY stage, a layout of the test positions P is plotted on a PC. When positioning the sample S, an amount of displacement necessary to dispose the desired test positions P in a position where the indentation will be formed is computed automatically by the PC. The XY stage is thus automatically displaced to position the sample S.

However, when performing the hardness test with the hardness tester that includes a manual XY stage, the user must compute the amount of displacement by him- or herself, thus incurring time and effort. When the XY stage is manually displaced, an amount of displacement of the XY stage cannot be readily recognized. Therefore, work to displace the XY stage by the calculated amount of displacement is difficult.

SUMMARY OF THE INVENTION

The present invention provides a hardness tester capable of facilitating positioning of a sample even when the hardness tester includes a manual XY stage.

One aspect of the present invention is a hardness tester measuring hardness of a sample placed on a sample stage by loading a predetermined test force on a surface of the sample with an indenter to form an indentation in the surface, then measuring dimensions of the indentation. The hardness tester includes an XY stage, an image capturer, a display, a test position specifier, and a controller. The XY stage displaces the sample stage in a horizontal direction. The image capturer captures an image of the surface of the sample via a objective lens. The display displays the image of the surface of the sample captured by the image capturer. The test position specifier specifies a test position at which the indentation is to be formed, the test position being specified on the image displayed on the display. The controller calculates, in conjunction with displacement of the XY stage, an amount of offset in the horizontal direction between the test position and a center position of the indenter when forming the indentation, then displaying the calculated amount of offset on the display.

Another aspect of the present invention is the hardness tester, in which the controller causes a notifier to perform notification of proximity in a distance between the test position and the center position of the indenter, based on the calculated amount of offset.

Another aspect of the present invention is the hardness tester, in which the controller causes the notifier to perform notification that the test position has reached the center position of the indenter when the calculated amount of offset is zero.

Another aspect of the present invention is the hardness tester, in which the controller causes the notifier to perform notification that displacement is in an opposite direction when the controller determines that the test position is moving away from the center position of the indenter based on the calculated amount of offset.

The present invention is capable of displaying an amount by which an XY stage must be displaced for a test position on a sample, which is to be disposed in a position of an indenter forming an indentation, the amount by which the XY stage must be displaced being displayed in real time on a display in conjunction with displacement of the XY stage. Therefore, even when the XY stage is a manual XY stage, the sample can be positioned easily.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description is taken with the drawings making apparent to those skilled in the art how the forms of the present invention may be embodied in practice.

Hereafter, an embodiment of the present invention is described with reference to the drawings. Moreover, in the following description, an X direction is a left-right direction, a Y direction is a front-back direction, and a Z direction is an up-down direction, with reference to FIG. 1. In addition, an X-Y plane is a horizontal plane.

Figure 1:
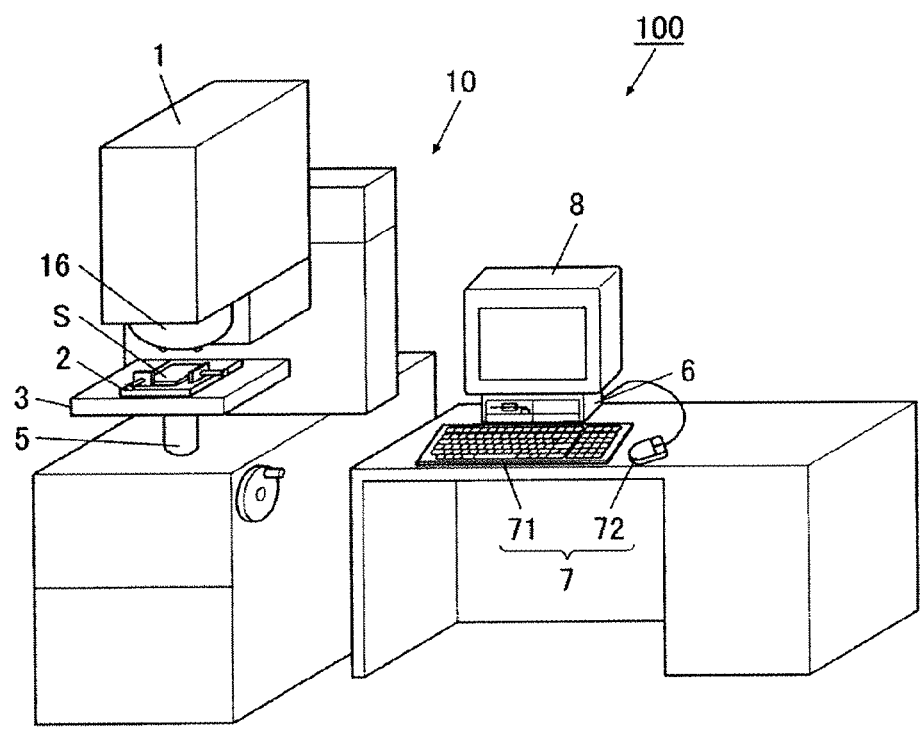
FIG. 1 is a perspective view illustrating an overall configuration of a hardness tester according to the present invention.
Figure 2:
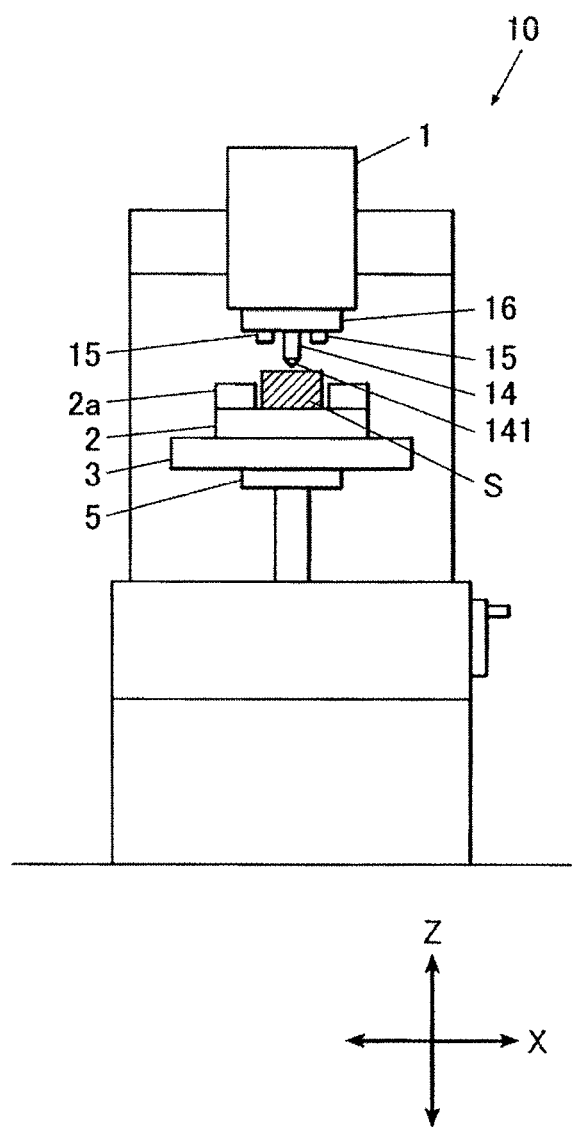
FIG. 2 is a schematic view illustrating a tester main body of the hardness tester according to the present invention.

A hardness tester 100 according to the present embodiment is a Vickers hardness tester, for example, and includes a tester main body 10, a controller 6, an operator 7, and a monitor 8, as shown in FIGS. 1 and 2.

The tester main body 10 includes a hardness measurer 1 performing a measurement of hardness of a sample S; a sample stage 2 on which the sample S is placed; an XY stage 3 displacing the sample stage 2 in the horizontal direction; and an elevator mechanism 5 raising and lowering the sample stage 2 and the XY stage 3 in a vertical direction so as to focus on a surface of the sample S.

Figure 3:
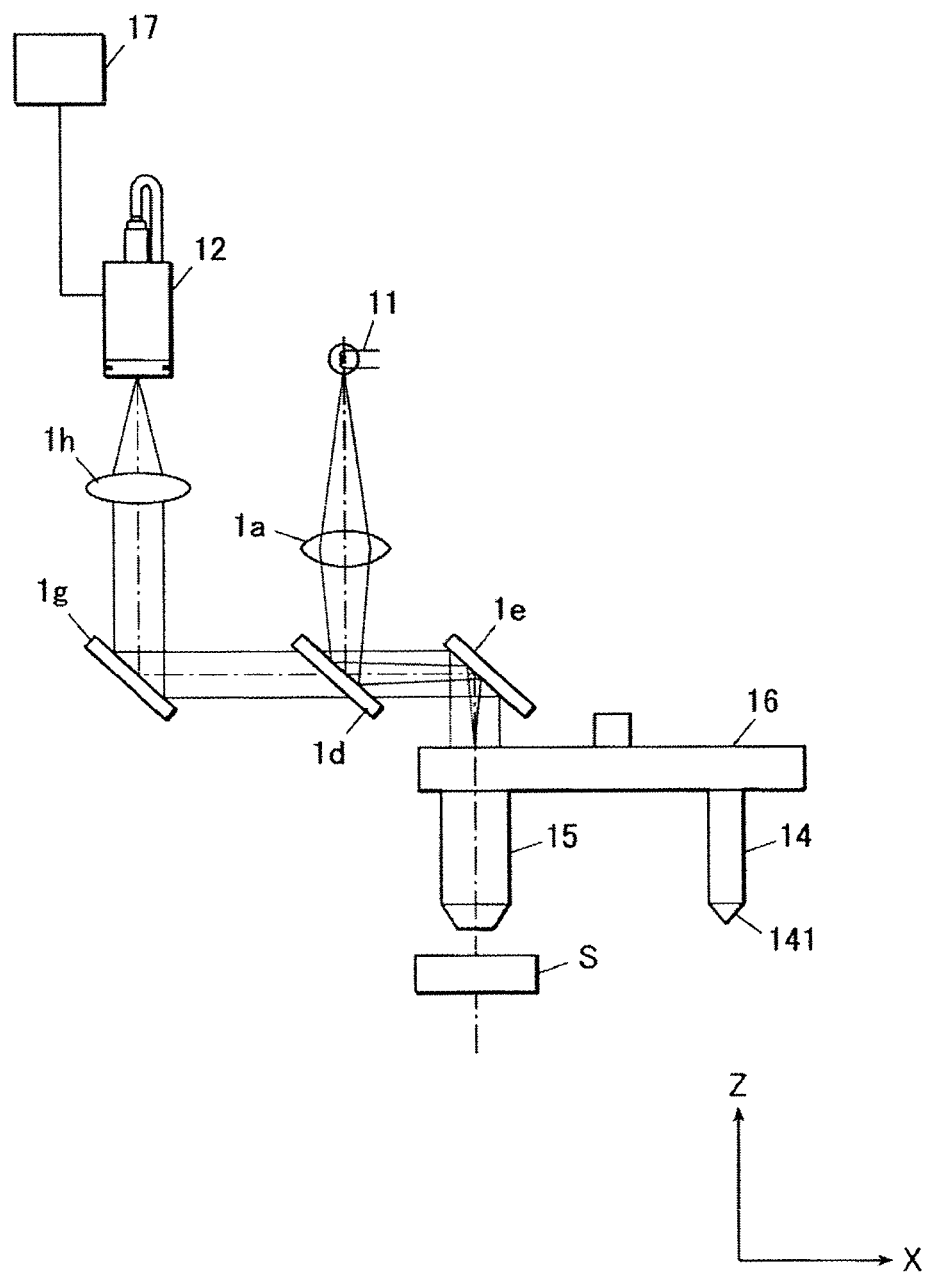
FIG. 3 is a schematic view illustrating a hardness measurer of the hardness tester according to the present invention.

As shown in FIG. 3, the hardness measurer 1 is configured with an illuminating device 11 illuminating the surface of the sample S; a CCD camera 12 capturing an image of the surface of the sample S; and a turret 16. The turret 16 includes an indenter axis 14, which includes an indenter 141, and a objective lens 15. The turret 16 is capable of switching between the indenter axis 14 and the objective lens 15 by rotating.

The illuminating device 11 shines a light to illuminate the surface of the sample S. The light shone by the illuminating device 11 reaches the surface of the sample S via a lens 1a, a half mirror 1d, a mirror 1e, and the objective lens 15.

Based on reflected light input from the surface of the sample S via the objective lens 15, the mirror 1e, the half mirror 1d, a mirror 1g, and a lens 1h, the CCD camera 12 obtains image data by capturing an image of the surface of the sample S as well as an indentation formed in the surface of the sample S by the indenter 141. The CCD camera 12 then outputs the image data to the controller 6 via a frame grabber 17, which is capable of simultaneously accumulating and storing a plurality of frames of image data. Thus, the CCD camera 12 is an image capturer.

A plurality of indenter axes 14 are held on a bottom surface of the turret 16 and are disposed above the sample S by rotating the turret 16. Thereby, the indenter axis 14 is displaced toward the sample S placed on the sample stage 2 by a load mechanism (not shown in the drawings), which is driven in response to a control signal output by the controller 6. The indenter axis 14 thus presses the indenter 141 against the surface of the sample S with a predetermined test force, the indenter 141 being provided on a tip of the indenter axis 14 and having a quadrangular pyramid diamond tip.

The objective lenses 15 are collective lenses each configured with a different magnification. A plurality of the objective lenses 15 are held on the bottom surface of the turret 16 and are disposed above the sample S by rotating the turret 16. Thereby, the light shone by the illuminating device 11 uniformly illuminates the surface of the sample S.

The turret 16 is configured so as to be capable of switching to and disposing above the sample S any one of the plurality of indenter axes 14 and the plurality of objective lenses 15, which are attached to the bottom surface of the turret 16, by rotating the turret 16 around a Z-axis direction. Specifically, the indentation can be formed in the surface of the sample S by disposing the indenter axis 14 above the sample S, and the formed indentation can be observed by disposing the objective lens 15 above the sample S.

The sample S is placed on an upper surface of the sample stage 2 and fixed in place with a sample holder 2a. The XY stage 3 is manually driven by a user and displaces the sample stage 2 in a direction (X-axis or Y-axis direction) perpendicular to a displacement direction (Z-axis direction) of the indenter 141 (i.e., in the horizontal direction). The elevator mechanism 5 is manually driven by the user and raises and lowers the sample stage 2 and the XY stage 3 in the vertical direction (the Z-axis direction), thereby changing a relative distance between the sample stage 2 and the objective lens 15.

The operator 7 is configured with a keyboard 71 and a mouse 72. The operator 7 executes an input operation by the user when performing a hardness test. In addition, when a predetermined input operation is performed by the operator 7, a predetermined operation signal corresponding to the input operation is output to the controller 6.

For example, the operator 7 enables the user to input a test condition value when carrying out the hardness test with the hardness tester 100. In addition, the input test condition value is transmitted to the controller 6. Herein, the test condition value is a value such as a material of the sample S, a test force (N) loaded on the sample S by the indenter 141, or a magnification power of the objective lens 15, for example. In addition, the operator 7 enables the user to specify a test position where the indentation is to be formed, the test position being specified on the image of the surface of the sample S displayed on the monitor 8. Thus, the operator 7 is a test position specifier.

The monitor 8 is configured with a display device such as an LCD, for example. The monitor 8 displays, for example, settings of the hardness test input on the operator 7, a layout for the test positions, results of the hardness test, and an image of the surface of the sample S as well as the indentation formed in the surface of the sample S captured by the CCD camera 12. Thus, the monitor 8 is a display.

Figure 4:
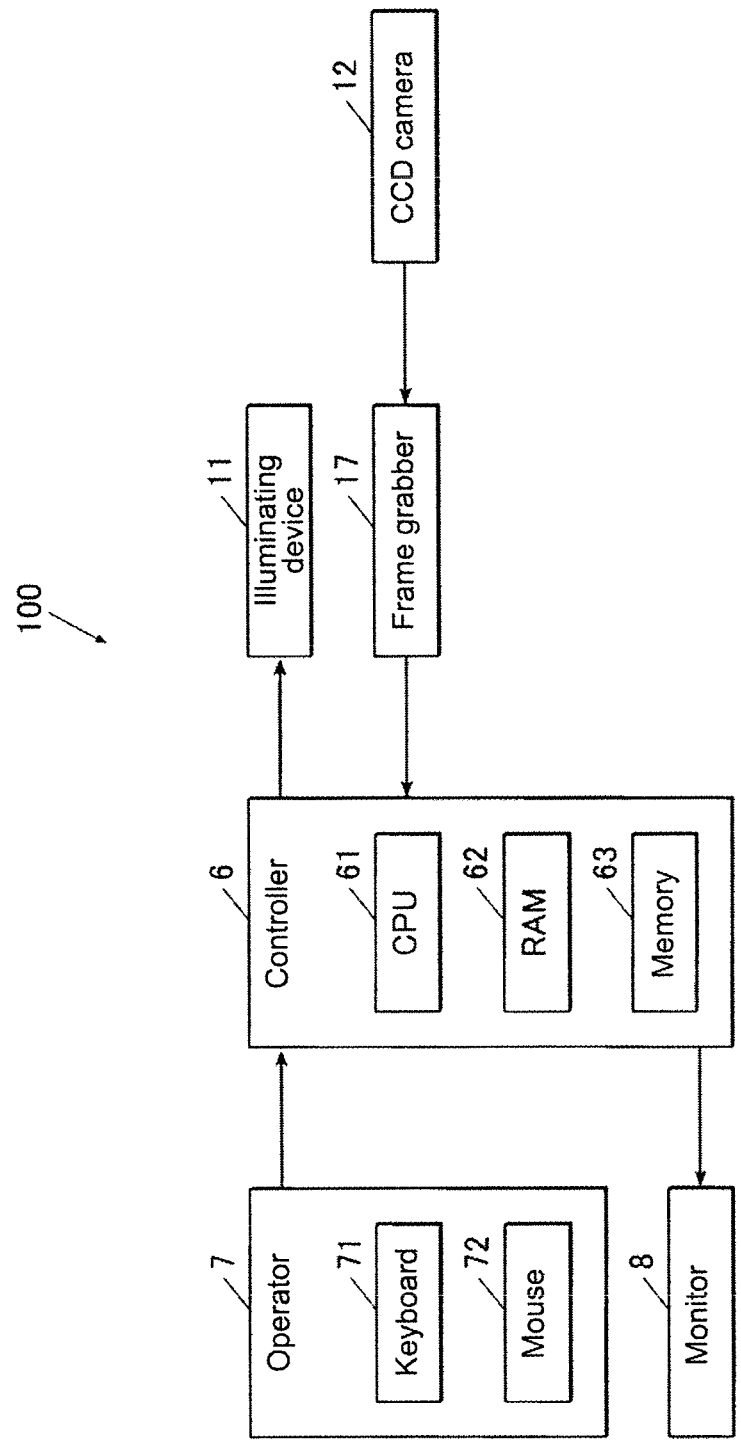
FIG. 4 is a block diagram illustrating a control structure of the hardness tester according to the present invention.

As shown in FIG. 4, the controller 6 is configured to include a CPU (Central Processing Unit) 61, a RAM (Random Access Memory) 62, and a memory 63. The controller 6 performs operation control for performing a predetermined hardness test by executing a predetermined program stored in the memory 63.

The CPU 61 retrieves a processing program stored in the memory 63, then opens and executes the processing program in the RAM 62. The CPU 61 thus performs overall control of the hardness tester 100.

The RAM 62 opens the processing program executed by the CPU 61 in a program storage region within the RAM 62 and stores input data as well as processing results generated when the processing program is executed in a data storage region.

The memory 63 includes, for example, a recording medium (not shown in the drawings) storing a program, data, and the like. The recording medium is configured with a semiconductor memory. In addition, the memory 63 stores various kinds of data allowing the CPU 61 to perform overall control of the hardness tester 100, various kinds of processing programs, and data processed by running the programs.

Figure 5:
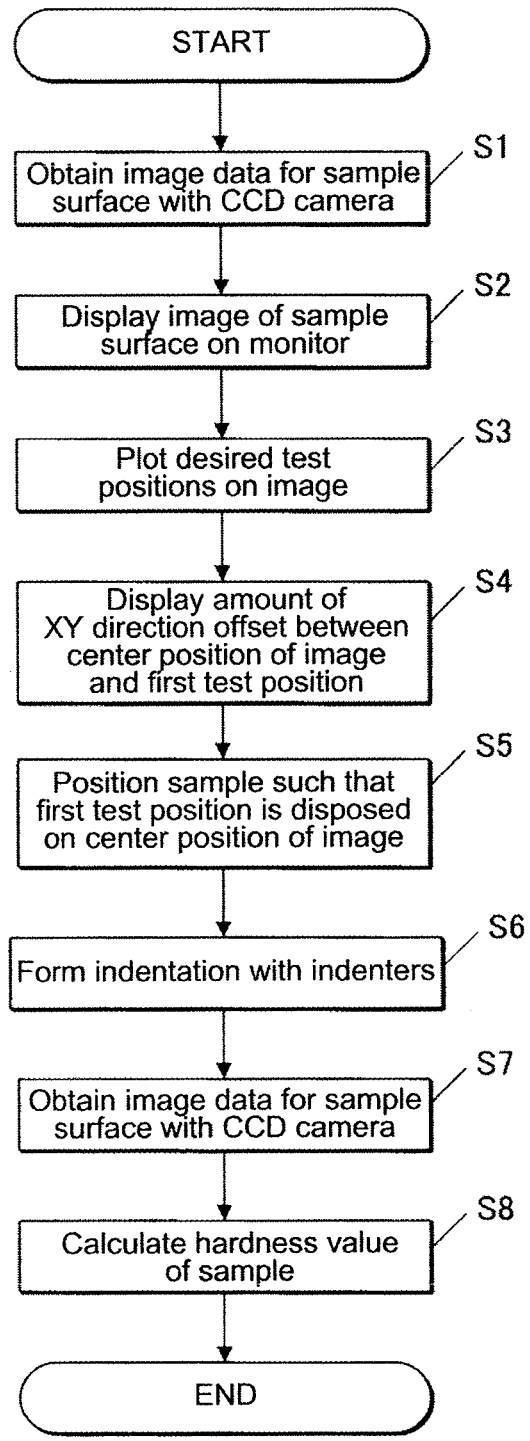
FIG. 5 is a flow chart illustrating operations of the hardness tester according to the present invention.

Next, operations of the hardness tester 100 according to the present embodiment are described with reference to a flow chart in FIG. 5. First, the image data for the surface of the sample S is obtained by the CCD camera 12 (step S1). Specifically, the user places the sample S undergoing the hardness test on the sample stage 2 and fixes the sample S in place with the sample holder 2a. The user then rotates the turret 16 to dispose the objective lens 15 above the sample S. The CCD camera 12 captures an image of the surface of the sample S via the objective lens 15 to obtain the image data, then outputs the image data to the controller 6.

Figure 6:
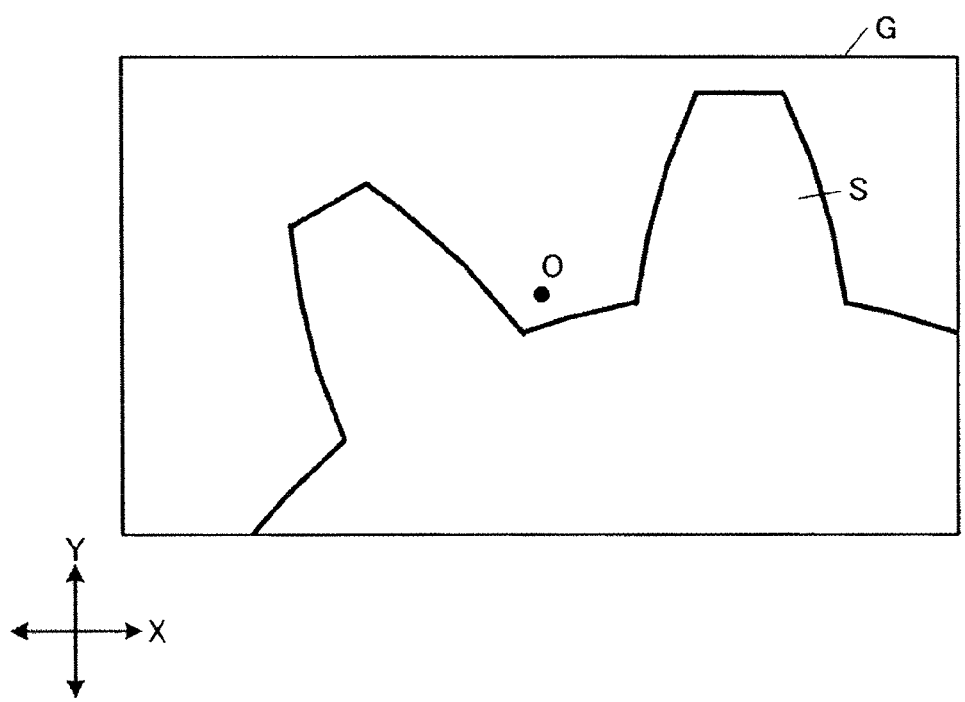
FIG. 6 illustrates an example of an image of a surface of a sample displayed on a monitor.

Next, the image of the surface of the sample S is displayed on the monitor 8 (step S2). Specifically, the CPU 61 displays an image G of the surface of the sample S on the monitor 8 based on the image data for the surface of the sample S output from the CCD camera 12 (see FIG. 6).

Figure 7:
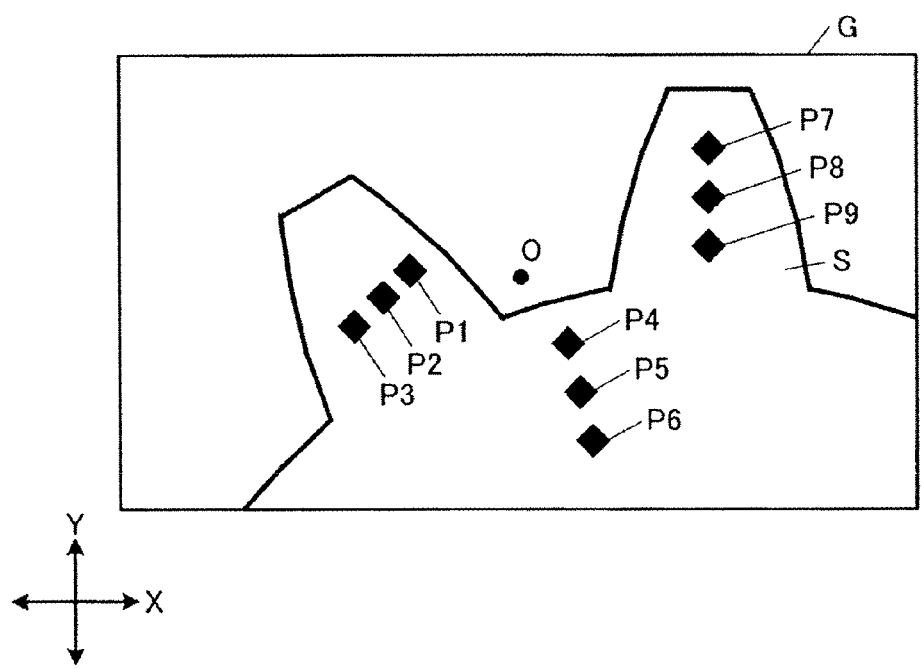
FIG. 7 illustrates an example of test positions plotted on the image of FIG. 6.

Next, the desired test positions are plotted on the image G (step S3). Specifically, the user operates the operator 7 to specify desired test positions P1, P2, and so on where the indentation is to be formed, the test positions P1, P2, and so on being specified on the image G of the surface of the sample S displayed on the monitor 8 (see FIG. 7). When specification of all the test positions P1, P2, and so on is complete, the user operates the operator 7 to input an instruction that specification of the test positions is complete.

Figure 8:
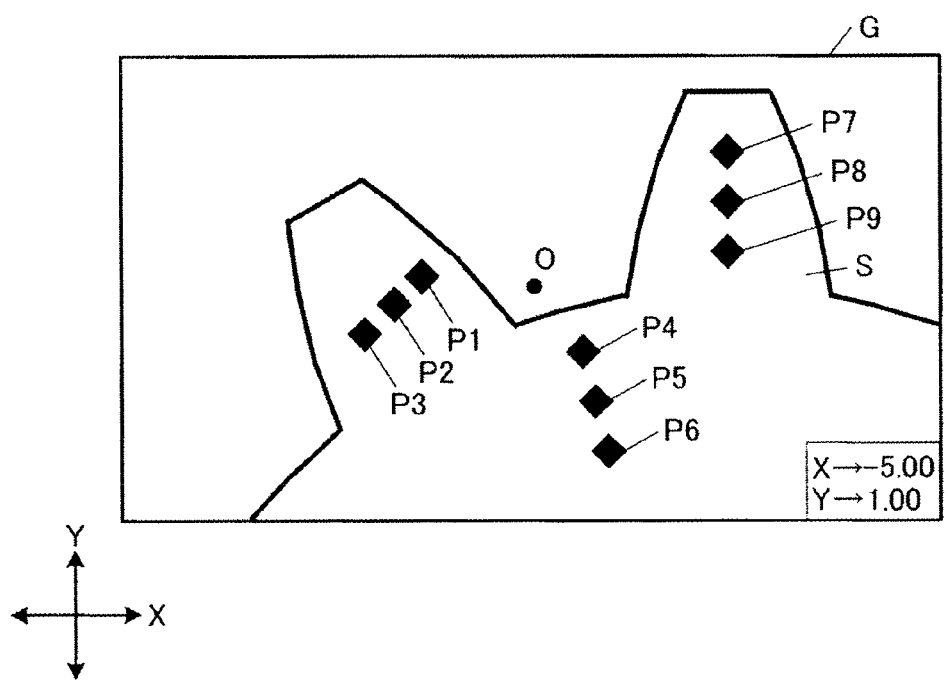
FIG. 8 illustrates an example of an amount of displacement for an XY stage necessary for a first test position to be disposed in a center position of the image, the displacement amount being displayed on the image of FIG. 7.

Next, an amount of offset in the XY direction (horizontal direction) between a center position O on the image G and the first test position P1 is displayed (step S4). Specifically, when the operation signal corresponding to the input operation (the instruction that specification of the test positions is complete) is received from the operator 7, the CPU 61 calculates the amount of offset in the XY direction between the first desired test position P1 and the center position O on the image G, which is the center position of the indenter 141 when forming the indentation in the sample S. The calculated amount of offset, i.e., the amount by which the XY stage 3 must be displaced in order for the first test position P1 to be disposed in the center position O on the image G, is displayed on the monitor 8 (see FIG. 8). For example, in the example shown in FIG. 8, the display indicates that the first test position P1 is offset "−5.00" in the X direction and "1.00" in the Y direction from the center position O on the image G. Specifically, the CPU 61 is a controller calculating the amount of offset in the XY direction between the test positions P1, P2, and so on and the center position of the indenter 141 when forming the indentation, the amount of offset being calculated in conjunction with displacement of the XY stage 3, and displaying the calculated amount of offset on the monitor 8.

Figure 9:
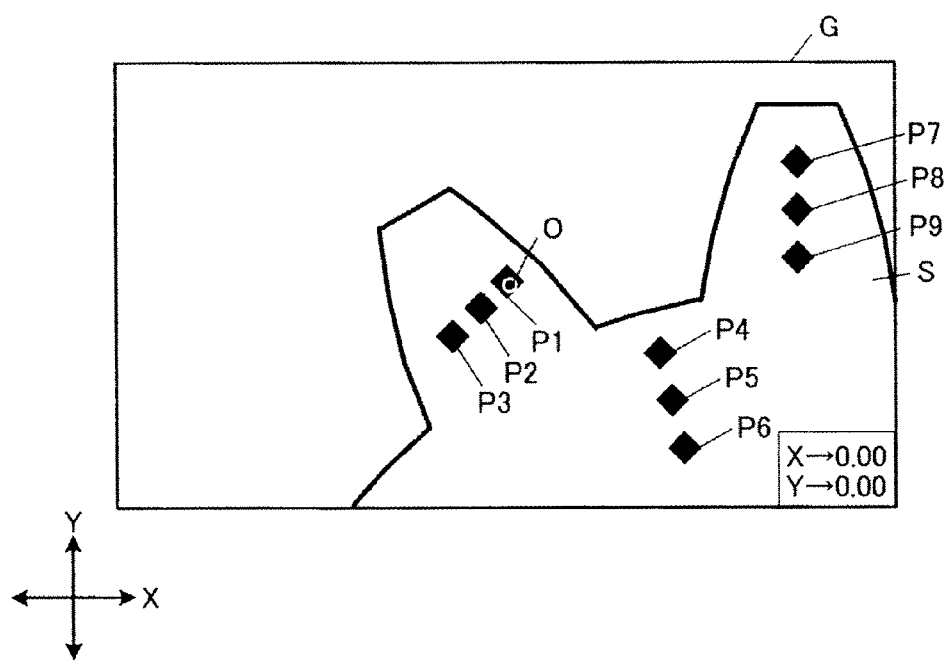
FIG. 9 illustrates an example of the sample displaced from the state of FIG. 8 such that the first test position is disposed in the center position of the image.
Figure 10:
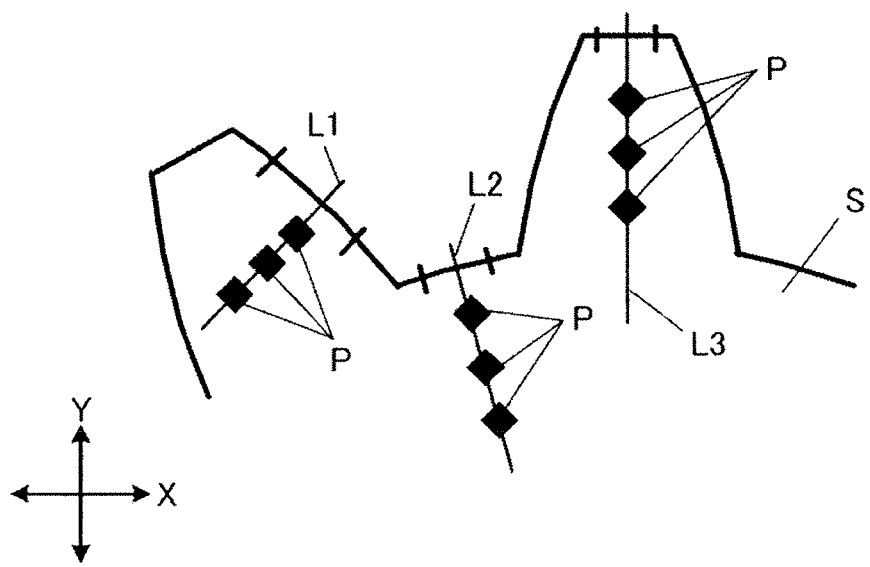
FIG. 10 illustrates an example of specified test positions in a conventional hardness tester.

Next, the sample S is positioned such that the first test position P1 is disposed on the center position O on the image G (step S5). Specifically, the user references the amount of offset in the XY direction displayed in step S4, then displaces the XY stage 3 in the XY direction. At this point, the CPU 61 continuously calculates the amount of offset in the XY direction between the first test position P1 and the center position O on the image G, then displays the calculated amount of offset in the XY direction on the monitor 8 in real time. Then, the user displaces the XY stage 3 until reaching a position where the amount of displacement in the XY direction is "0" in both the X and Y directions (see FIG. 9).

Next, the indentation is formed by the indenter 141 in the first test position P1 (step S6). Specifically, the user rotates the turret 16 to dispose the indenter 141 above the sample S, then operates the operator 7 to input an indentation instruction. When the CPU 61 receives the operation signal corresponding to the input operation from the operator 7, the load mechanism is driven, thereby lowering the indenter 141 and forming the indentation in the first test position P1. Thereafter, indentations are formed at the remaining test positions P2 and so on by repeating the processes of steps S4 to S6 such that indentations are formed at all of the test positions P1, P2, and so on.

Next, the image data for the surface of the sample S is obtained by the CCD camera 12 (step S7). Specifically, the user rotates the turret 16 to dispose the objective lens 15 above the sample S. The CCD camera 12 captures the image of the surface of the sample S via the objective lens 15 to obtain the image data, then outputs the image data to the controller 6.

Next, based on the indentation formed in the surface of the sample S, a degree of hardness of the sample S is calculated (step S8). Specifically, the CPU 61 analyzes the image data for the surface of the sample S output from the CCD camera 12, then measures a length of diagonal lines in the indentation formed in the surface of the sample S. The CPU 61 then calculates the hardness value for the sample S based on the measured length of the diagonal lines.

As described above, the hardness tester 100 according to the present embodiment includes the XY stage 3 displacing the sample stage 2 in the horizontal direction; the CCD camera 12 capturing the image of the surface of the sample S via the objective lens 15; the monitor 8 displaying the image G of the surface of the sample S captured by the CCD camera 12; the operator 7 specifying the test positions P1, P2, and so on where the indentation is to be formed, the test positions P1, P2, and so on being specified on the image G displayed on the monitor 8; and the CPU 61 calculating the amount of offset in the XY direction between the test positions P1, P2, and so on and the center position of the indenter 141 when forming the indentation, the amount of offset being calculated in conjunction with displacement of the XY stage 3, and displaying the calculated amount of offset on the monitor 8. Therefore, the amount of displacement necessary for the test positions P1, P2, and so on on the sample S to be disposed at the position of the indenter 141 forming the indentation can be displayed on the monitor 8 in real time in conjunction with displacement of the XY stage 3. Thus, even when the XY stage 3 is a manual XY stage 3, the sample S can be positioned easily.

Above, a concrete description was given based on an embodiment according to the present invention. However, the present invention is not limited to the above-described embodiment and may be modified within a scope not deviating from the substance of the invention.

FIRST MODIFICATION EXAMPLE

For example, in the above-described embodiment, the amount of offset in the XY direction between the desired test positions P1, P2, and so on and the center position O on the image G, which is the center position of the indenter 141 when forming the indentation in the sample S, is calculated, then the calculated amount of offset is displayed on the monitor 8. However, in addition, based on the calculated amount of offset described above, the user may also be notified of proximity in a distance between the desired test positions P1, P2, and so on and the center position O on the image G through a control of the CPU 61.

For example, when the desired test positions P1, P2, and so on have approached within a predetermined distance to the center position O on the image G, the amount of offset may be displayed in red and when the desired test positions P1, P2, and so on have moved away to a predetermined distance or greater from the center position O on the image G, the amount of offset may be displayed in blue. In such a case, the monitor 8 is a notifier. In addition, a speaker (not shown in the drawings) or the like may be provided capable of sound output. Then, when the desired test positions P1, P2, and so on are within the predetermined distance, a voice may be output saying "You are almost to the target," and when the desired test positions P1, P2, and so on have moved away to the predetermined distance or greater, the voice may be output saying "You have moved away from the target." In such a case, the speaker is the notifier. In addition, the XY stage 3 may be vibrated when the desired test positions P1, P2, and so on are within the predetermined distance, and the load placed on the XY stage 3 during displacement may be increased when the desired test positions P1, P2, and so on have moved away to the predetermined distance or greater. In such a case, the XY stage 3 is the notifier. Moreover, the combinations of color, sound, and feedback described above are merely exemplary and may be modified as appropriate within a range capable of notifying the user of the proximity.

As described above, according the hardness tester 100 according to the first modification example, the CPU 61 notifies the user of the proximity in the distance between the desired test positions P1, P2, and so on and the center position of the indenter 141 (the center position O on the image G) using the notifier (the monitor 8, the speaker, the XY stage 3) based on the calculated amount of offset. Therefore, the user can recognize the proximity in the distance to the target while displacing the XY stage 3. Thus, the sample S can be positioned more easily.

SECOND MODIFICATION EXAMPLE

In the first modification example described above, the user is notified of the proximity in the distance between the desired test positions P1, P2, and so on and the center position of the indenter 141 (the center position O on the image G). However, in addition, when the calculated amount of offset is zero, the user may be notified that the desired test positions P1, P2, and so on have reached the center position O on the image G through a control of the CPU 61.

For example, when the calculated amount of offset is zero, a character "0" displayed on the monitor 8 may be displayed in yellow. Alternatively, the character "0" may flash. In addition, when the calculated amount of offset is zero, the voice may be output saying "You have reached the target position." In addition, when the calculated amount of offset is zero, the XY stage 3 may lock. Moreover, the color, sound, and feedback described above are merely exemplary and may be modified as appropriate within a range capable of notifying the user that the target has been reached.

As described above, according to the hardness tester 100 according to the second modification example, when the calculated amount of offset is zero, the CPU 61 notifies the user that the desired test positions P1, P2, and so on have reached the center position of the indenter 141 using the notifier (the monitor 8, the speaker, the XY stage 3). Therefore, the user can recognize that the target has been reached while displacing the XY stage 3. Thus, the sample S can be positioned more easily.

THIRD MODIFICATION EXAMPLE

In the first modification example described above, the user is notified of the proximity in the distance between the desired test positions P1, P2, and so on and the center position of the indenter 141 (the center position O on the image G). In the second modification example described above, the user is notified that the desired test positions P1, P2, and so on have reached the center position O on the image G. However, in addition, when the CPU 61 determines that the desired test positions P1, P2, and so on are moving away from the center position O on the image G based on the calculated amount of offset, the user may be notified that displacement is in the opposite direction, for example, through a control of the CPU 61.

For example, when the CPU 61 determines that the desired test positions P1, P2, and so on are moving away from the center position O on the image G, the amount of offset displayed on the monitor 8 may be displayed in green. Alternatively, the amount of offset may be erased from the display. In addition, when the CPU 61 determines that the desired test positions P1, P2, and so on are moving away from the center position O on the image G, the voice may be output saying "The target is in the opposite direction." In addition, when the CPU 61 determines that the desired test positions P1, P2, and so on are moving away from the center position O on the image G, the load placed on the XY stage 3 during displacement may be increased. Moreover, the color, sound, and feedback described above are merely exemplary and may be modified as appropriate within a range capable of notifying the user that displacement is in the opposite direction.

As described above, according to the hardness tester 100 according to the third modification example, when the CPU 61 determines that the desired test positions P1, P2, and so on are moving away from the center position of the indenter 141 based on the calculated amount of offset, the CPU 61 notifies the user that displacement is in the opposite direction using the notifier (the monitor 8, the speaker, the XY stage 3). Therefore, the user can recognize that the XY stage 3 is being operated in the wrong direction while displacing the XY stage 3. Thus, the sample S can be positioned efficiently. Moreover, the first through third modification examples may each be used in isolation or may be combined, as desired.

In addition, the Vickers hardness tester was described to exemplify the hardness tester 100 in the above-described embodiment. However, the present invention is not limited to this. For example, the present invention may be applied to a Knoop hardness tester having an indenter with a rhomboid pyramid diamond indenter, or to a Brinell hardness tester having a spherical indenter.

In addition, within a scope not deviating from the substance of the present invention, appropriate modifications may also be made to detailed structures and operations of each component configuring the hardness tester 100.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular structures, materials and embodiments, the present invention is not intended to be limited to the particulars disclosed herein; rather, the present invention extends to all functionally equivalent structures, methods and uses, such as are within the scope of the appended claims.

The present invention is not limited to the above described embodiments, and various variations and modifications may be possible without departing from the scope of the present invention.

What is claimed is:

1. A hardness tester measuring hardness of a sample placed on a sample stage by loading a predetermined test force on a surface of the sample with an indenter to form an indentation in the surface, then measuring dimensions of the indentation, the hardness tester comprising:
    an XY stage configured to displace the sample stage in a horizontal direction;
    an image capturer configured to capture an image of the surface of the sample via a objective lens;
    a display configured to display the image of the surface of the sample captured by the image capturer;
    a test position specifier configured to specify a test position at which the indentation is to be formed, the test position being specifiable on the image displayed on the display; and
    a controller configured to calculate, in conjunction with displacement of the XY stage, an amount of offset in the horizontal direction between the test position and a center position of the indenter when forming the indentation, then to display the calculated amount of offset on the display.

2. The hardness tester according to claim 1, wherein the controller is further configured to cause a notifier to perform notification of proximity in a distance between the test position and the center position of the indenter, based on the calculated amount of offset.

3. The hardness tester according to claim 1, wherein the controller is further configured to cause the notifier to perform notification that the test position has reached the center position of the indenter when the calculated amount of offset is zero.

4. The hardness tester according to claim 2, wherein the controller is further configured to cause the notifier to perform notification that the test position has reached the center position of the indenter when the calculated amount of offset is zero.

5. The hardness tester according to claim 1, wherein the controller is further configured to cause the notifier to perform notification that displacement is in an opposite direction when the controller determines that the test position is moving away from the center position of the indenter, based on the calculated amount of offset.

6. The hardness tester according to claim 2, wherein the controller is further configured to cause the notifier to perform notification that displacement is in an opposite direction when the controller determines that the test position is moving away from the center position of the indenter, based on the calculated amount of offset.

7. The hardness tester according to claim 3, wherein the controller is further configured to cause the notifier to perform notification that displacement is in an opposite direction when the controller determines that the test position is moving away from the center position of the indenter, based on the calculated amount of offset.

8. The hardness tester according to claim 4, wherein the controller is further configured to cause the notifier to perform notification that displacement is in an opposite direction when the controller determines that the test position is moving away from the center position of the indenter, based on the calculated amount of offset.

* * * * *